United States Patent [19]

Hendriksen et al.

[11] Patent Number: 6,111,157
[45] Date of Patent: *Aug. 29, 2000

[54] AROMATIC CONVERSION PROCESSES AND ZEOLITE BOUND ZEOLITE CATALYST USEFUL THEREIN

[75] Inventors: Dan Eldon Hendriksen, Kingwood; Gary David Mohr, League City, both of Tex.; Johannes Petrus Verduijn, Rotterdam, Netherlands; Robert Scott Smith, Houston, Tex.

[73] Assignee: Exxon Chemical Patents, Inc., Houston, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/865,633

[22] Filed: May 29, 1997

Related U.S. Application Data

[60] Provisional application No. 60/018,390, May 29, 1996.

[51] Int. Cl.$^7$ .............................. C07C 2/68; C07C 5/22; B01J 24/06
[52] U.S. Cl. ................... 585/467; 585/475; 585/481; 502/67
[58] Field of Search ........................ 585/467, 67, 475, 585/481

[56] References Cited

U.S. PATENT DOCUMENTS

| | | | |
|---|---|---|---|
| 4,169,111 | 9/1979 | Wright | 58/323 |
| 4,381,256 | 4/1983 | Hildebrandt | 252/455 Z |
| 4,582,815 | 4/1986 | Bowes | 502/64 |
| 4,783,568 | 11/1988 | Schmidt | 585/477 |
| 4,847,224 | 7/1989 | Fajula, et al. | 502/67 |
| 4,902,843 | 2/1990 | Onodera et al. | 585/481 |
| 5,145,659 | 9/1992 | McWilliams | 423/328 |
| 5,430,211 | 7/1995 | Pogue et al. | 585/323 |

FOREIGN PATENT DOCUMENTS

| | | |
|---|---|---|
| 11059/35 | 8/1992 | China . |
| 0109962 | 6/1984 | European Pat. Off. . |
| 0110650 | 6/1984 | European Pat. Off. . |
| 0284206 | 9/1988 | European Pat. Off. . |
| 0323892 | 12/1989 | European Pat. Off. . |
| 5-3063318 | 6/1978 | Japan . |
| 404253925 | 9/1992 | Japan . |
| WO92/12928 | 8/1992 | WIPO . |
| WO96/16004 | 5/1996 | WIPO . |

OTHER PUBLICATIONS

Chemical Abstracts, vol. 101, No. 9, Aug. 27, 1984 Columbus, Ohio, US; Abstract No. 72405n, p. 614.
Chemical Abstracts, vol. 85, No. 13, Sep. 27, 1976 Columbus, Ohio, US; Abstract No. 94018s, p. 604.
Internet Serch document; web site address: http://www.iza-sc.ethz.ch/IZA-SC/Atlas/data, Jan. 14, 1999.
U.S. Patent application No. 08/561,674, filed Nov. 22, 1995.
U.S. Patent application No. 08/865,632, filed May 29, 1997.

*Primary Examiner*—Walter D. Griffin
*Assistant Examiner*—Thuan D. Dang
*Attorney, Agent, or Firm*—Edward F. Sherer

[57] ABSTRACT

A process is provided for the alkylation, transalkylation, or isomerization of aromatic hydrocarbons. The processes comprises contacting aromatic hydrocarbons under conversion conditions with a zeolite bound zeolite catalyst. The zeolite bound zeolite catalyst comprises first crystals of a first large pore zeolite which are bound together by second crystals of a second zeolite.

51 Claims, 1 Drawing Sheet

AROMATIC CONVERSION PROCESSES AND ZEOLITE BOUND ZEOLITE CATALYST USEFUL THEREIN

This application claims the benefit of U.S. Provisional Application Ser. No. 60/018,390, filed May 29, 1996.

FIELD OF THE INVENTION

This invention relates to the isomerization, alkylation, and/or transalkylation of aromatic hydrocarbons using zeolite bound zeolite catalysts.

BACKGROUND OF THE INVENTION

Various processes comprising alkylation and/or transalkylation are known to produce monoalkylaromatic products such as isopropylbenzene, which is also known as cumene, or ethylbenzene in high yields. However, such processes are not without problems including the production of undesirable by-products. Examples of such by-products produced in conjunction with cumene include alkylating agent oligomers, heavy polyaromatic compounds and unwanted monoalkylated and dealkylated compounds such as n-propylbenzene, butylbenzenes and ethylbenzene. The production of unwanted xylenes is a particular problem in the production of ethylbenzene. Another problem with such processes concerns the use of Friedel Crafts catalysts such as solid phosphoric acid or aluminum chloride. The phosphoric acid catalysts generally require the use of a water co-feed which produces corrosive sludge by-product. Problems concerning the sludge by-product can be avoided by the use of certain crystalline microporous molecular sieves as catalysts. However, major drawbacks of the use of zeolite catalysts include the production of undesirable by-products and relatively rapid deactivation of the catalyst requiring timely and costly replacement or reactivation.

Crystalline microporous molecular sieves are ordered, porous, crystalline material having a definite crystalline structure as determined by x-ray diffraction, within which there are a large number of smaller cavities which may be interconnected by a number of still smaller channels or pores. The dimensions of these pores are such as to allow for adsorption of molecules with certain dimensions while rejecting those of large dimensions. The interstitial spaces or channels formed by the crystalline network enable molecular sieves such as crystalline silicates, crystalline aluminosilicates, crystalline silicoalumino phosphates, and crystalline aluminophosphates, to be used as molecular sieves in separation processes and catalysts and catalyst supports in a wide variety of hydrocarbon conversion processes.

Within a pore of the crystalline molecular sieve, hydrocarbon conversion reactions such the alkylation, and transalkylation of aromatics are governed by constraints imposed by the size of the molecular sieve. Reactant selectivity occurs when a fraction of the feedstock is too large to enter the pores to react; while product selectivity occurs when some of the products can not leave the channels or do not subsequently react. Product distribution can also be altered by transition state selectivity in which certain reactions can not occur because the reaction transition state is too large to form within the pores. Selectivity can also result from configuration constraints on diffusion where the dimensions of the molecule approach that of the pore system. Non-selective reactions on the surface of the molecular sieve are generally not desirable as such reactions are not subject to the shape selective constraints imposed on those reactions occurring within the channels of the molecular sieve.

Zeolites are comprised of a lattice of silica and optionally alumina combined with exchangeable cations such as alkali or alkaline earth metal ions. Although the term "zeolites" includes materials containing silica and optionally alumina, it is recognized that the silica and alumina portions may be replaced in whole or in part with other oxides. For example, germanium oxide, tin oxide, phosphorous oxide, and mixtures thereof can replace the silica portion. Boron oxide, iron oxide, titanium oxide, gallium oxide, indium oxide, and mixtures thereof can replace the alumina portion. Accordingly, the terms "zeolite", "zeolites" and "zeolite material", as used herein, shall mean not only materials containing silicon and, optionally, aluminum atoms in the crystalline lattice structure thereof, but also materials which contain suitable replacement atoms for such silicon and aluminum, such as gallosilicates, silicoaluminophosphates (SAPO) and aluminophosphates (ALPO). The term "aluminosilicate zeolite", as used herein, shall mean zeolite materials consisting essentially of silicon and aluminum atoms in the crystalline lattice structure thereof.

Numerous processes have been proposed for the isomerization, alkylation, or transalkylation of aromatic hydrocarbon. For instance, U.S. Pat. No. 4,312,790 involves a xylene isomerization process using an alumina bound zeolite catalyst. U.S. Pat. No. 5,227,558 involves an aromatic alkylation process using a zeolite beta catalyst bound by a binder such as aluminia.

Synthetic zeolites are normally prepared by the crystallization of zeolites from a supersaturated synthesis mixture. The resulting crystalline product is then dried and calcined to produce a zeolite powder. Although the zeolite powder has good adsorptive properties, its practical applications are severely limited because it is difficult to operate fixed beds with zeolite powder. Therefore, prior to using the powder in commercial processes, the zeolite crystals are usually bound.

The zeolite powder is typically bound by forming a zeolite aggregate such as a pill, sphere, or extrudate. The extrudate is usually formed by extruding the zeolite in the presence of a non-zeolitic binder and drying and calcining the resulting extrudate. The binder materials used are resistant to the temperatures and other conditions, e.g., mechanical attrition, which occur in various hydrocarbon conversion processes. Examples of binder materials include amorphous materials such as alumina, silica, titania, and various types of clays. It is generally necessary that the zeolite be resistant to mechanical attrition, that is, the formation of fines which are small particles, e.g., particles having a size of less than 20 microns.

Although such bound zeolite aggregates have much better mechanical strength than the zeolite powder, when such a bound zeolite is used for aromatics conversion, the performance of the zeolite catalyst, e.g., activity, selectivity, activity maintenance, or combinations thereof, can be reduced because of the binder. For instance, since the binder is typically present in an amount of up to about 50 wt. % of zeolite, the binder dilutes the adsorption properties of the zeolite aggregate. In addition, since the bound zeolite is prepared by extruding or otherwise forming the zeolite with the binder and subsequently drying and calcining the extrudate, the amorphous binder can penetrate the pores of the zeolite or otherwise block access to the pores of the zeolite, or slow the rate of mass transfer to the pores of the zeolite which can reduce the effectiveness of the zeolite when used in aromatic conversion processes. Furthermore, when the bound zeolite is used in aromatic conversion processes, the binder may affect the chemical reactions that are taking place within the zeolite and also may itself catalyze undesirable reactions which can result in the formation of undesirable products.

SUMMARY OF THE INVENTION

In one embodiment, the present invention is directed to aromatic conversion processes such as the isomerization, alkylation, and/or transalkylation of aromatic hydrocarbons using a zeolite bound zeolite catalyst. The zeolite bound zeolite catalyst comprises first crystals of a large pore first zeolite and a binder comprising second crystals of a second zeolite. The isomerization, alkylation, or isomerization of aromatic streams in accordance with the present invention gives rise to high yields of desired product.

In another embodiment, the present invention is directed to a zeolite bound zeolite catalyst which finds particular application in aromatic conversion processes and comprises first crystals of a first zeolite having a MOR, EMT, or MAZ structure type and a binder comprising second crystals of a second zeolite.

DETAILED DESCRIPTION OF THE INVENTION

Figure 1:
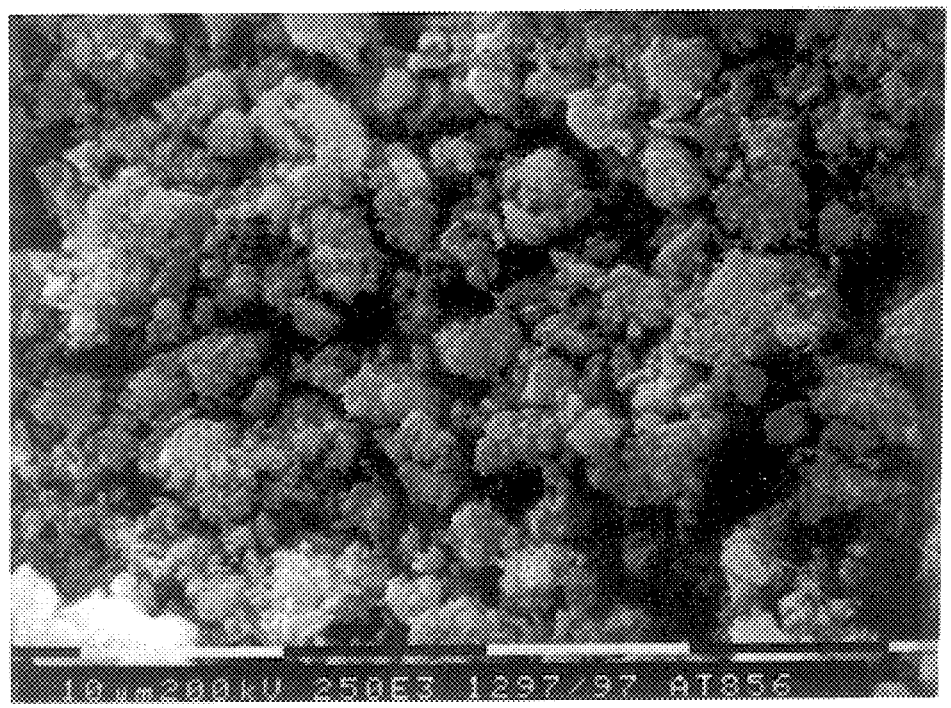
FIG. 1 shows SEM micrographs of the Catalyst of Example 1.

The zeolite bound zeolite catalyst comprises first crystals of an acidic large pore zeolite and a binder comprising second crystals of a second zeolite which preferably have an average particle size of less than said first particles. The use of the second zeolite crystals as a binder results in a catalyst which provides a means for controlling undesirable reactions taking place in or near the external surface of the first zeolite crystals and can have improved mass transfer of reactants and greater access to and from the pores of the first zeolite. In addition, the second zeolite binding crystals, if desired, can also have catalytic activity, can function as a catalyst carrier, and/or can selectively prevent undesirable molecules from entering or exiting the pores of the first zeolite.

Unlike typical zeolite catalysts used in hydrocarbon conversion processes which are normally bound with silica or alumina or other commonly used amorphous binders to enhance the mechanical strength of the zeolite, the zeolite catalyst of the present invention does not contain significant amounts of non zeolitic binders. Preferably, the zeolite catalyst contains less than 10 percent by weight based on the total weight of the first and second zeolite, of non-zeolitic binder, and more preferably contains less than 5 percent by weight, and, most preferably, the catalyst is substantially free of non-zeolitic binder. Preferably, the second zeolite crystals bind the first zeolite crystals by adhering to the surface of the first zeolite crystals thereby forming a matrix or bridge structure which also holds the first crystals particles together. More preferably, the second zeolite particles bind the first zeolite by intergrowing so as to form a coating or partial coating on the larger first zeolite crystals and, most preferably, the second zeolite crystals bind the first zeolite crystals by intergrowing to form an attrition resistant overgrowth over the first zeolite crystals.

Although the invention is not intended to be limited to any theory of operation, it is believed that one of the advantages of the zeolite catalyst system of the present invention is obtained by the second zeolite and thus controlling the accessibility of the acid sites on the external surfaces of the first zeolite to reactants. Since the acid sites existing on the external surface of a zeolite catalyst are not shape selective, these acid sites can adversely affect reactants entering the pores of the zeolite and products exiting the pores of the zeolite. In line with this belief, since the acidity of the second zeolite can be carefully selected, the second zeolite does not significantly adversely affect the reactants exiting the pores of the first zeolite which can occur with conventionally bound zeolite catalysts and may beneficially affect the reactants exiting the pores of the first zeolite. Still further, since the second zeolite is not amorphous but, instead, is a molecular sieve, hydrocarbons may have increased access to the pores of the first zeolite during hydrocarbon conversion processes. Regardless of the theories proposed, the zeolite bound zeolite catalyst when used in catalytic processes, has the improved properties which are disclosed herein.

The terms "acidity", "lower acidity" and "higher acidity" as applied to zeolite are known to persons skilled in the art. The acidic properties of zeolite are well known. However, with respect to the present invention, a distinction must be made between acid strength and acid site density. Acid sites of a zeolite can be a Bronsted acid or a Lewis acid. The density of the acid sites and the number of acid sites are important in determining the acidity of the zeolite. Factors directly influencing the acid strength are (i) the chemical composition of the zeolite framework, i.e., relative concentration and type of tetrahedral atoms, (ii) the concentration of the extra-framework cations and the resulting extra-framework species, (iii) the local structure of the zeolite, e.g., the pore size and the location, within the crystal or at/near the surface of the zeolite, and (iv) the pretreatment conditions and presence of co-adsorbed molecules. The amount of acidity is related to the degree of isomorphous substitution provided, however, such acidity is limited to the loss of acid sites for a pure $SiO_2$ composition. As used herein, the terms "acidity", "lower acidity" and "higher acidity" refers to the concentration of acid sites irregardless of the strength of such acid sites which can be measured by ammonia absorption.

The term "average particle size" as used herein, means the arithmetic average of the diameter distribution of the crystals on a volume basis.

Examples of large pore zeolites suitable for use in the zeolite bound zeolite catalyst include zeolites having a pore size of at least about 7.0 Å. These zeolites are described in "Atlas of Zeolite Structure Types", eds. W. H. Meier and D. H. Olson, Buttersworth-Heineman, Third Edition, 1992, which is hereby incorporated by reference. Examples of large pore include VFI, AFI, MAZ, MEI, FAU, EMT, OFF, BEA, and MOR structure type zeolites (IUPAC Commission of Zeolite Nomenclature). Examples of large pore zeolites include for example mazzite, offretite, zeolite L, VPI-5, zeolite Y, zeolite X, omega, Beta, ZSM-3, ZSM-4, ZSM-18, ZSM-20, and SAPO-37. The structure type of the first and second zeolite can be the same or different. The zeolites are usually at least partially in the hydrogen form. Preferred first zeolites are zeolites having BEA or MOR structure types.

As known to persons skilled in the art, the acidity of a zeolite can be reduced using many techniques such as steaming. In addition, the acidity of a zeolite is dependent upon the form of the zeolite with the hydrogen form having the highest acidity and other forms of the zeolite such as the sodium form having less acidity than the acid form. Accordingly, the mole ratios of silica to alumina disclosed herein shall include not only zeolites having the disclosed mole ratios, but shall also include zeolites not having the disclosed mole ratios but having equivalent catalytic activity.

Large pore size zeolites suitable for use in the zeolite bound zeolite catalyst generally comprise a composition having the following molar relationship:

$$X_2O_3:(n)YO_2,$$

wherein X is a trivalent element, such as aluminum, boron and/or gallium, Y is a tetravalent element such as silicon, tin, and/or germanium; and n has a value greater than 2, said value being dependent upon the particular type of zeolite and the trivalent element present in the zeolite.

When the first zeolite is an aluminosilicate zeolite, the silica to alumina ratio of the first zeolite will usually depend upon the structure type of the first zeolite and is therefore not limited to any particular ratio. Generally, however, and depending on the structure type of the zeolite, the first zeolite will have a silica to alumina mole ratio of at least 2:1, and may have a silica to alumina mole ratio to about 300:1. Preferably the aluminosilicate zeolite is in the hydrogen form.

The crystal size of the first crystals will preferably be in the range of from about at least about 0.1 micron to 15 microns. More preferably, the first crystals will have an average particle size from 1 to 6 microns. The use of large crystals is desired because the use of large crystals decreases the specific outer crystal surface area which in turn results in an increase in the ratio of intracrystalline acid sites to surface acid sites.

Procedures to determine crystal size are known to persons skilled in the art. For instance, crystal size may be determined directly by taking a suitable scanning electron microscoped (SEM) picture of a representative same of the crystals.

The external surface acidity of the large size first crystals of the first zeolite is preferably less than acidity within the channels of the zeolite. The external surface acidity is preferably at least 40% less than the acidity within the channels and, more preferably at least 50% less and even more preferably is at least 60% less. Most preferably, the first crystals are substantially free of surface acidity.

Procedures for reducing the surface acidity of the first crystals include the dealumination of the zeolite surface by hydrothermal, acid, or chemical treatments. For example, the surface acidity of the first crystals can be reduced by treating the surface of the crystals with basic compounds such as amines, phosphines, phenols, polynuclear hydrocarbons, cationic dyes, and the like. In addition, the surface acidity of the crystals can be reduced by depositing on the surface of the crystals a material such as a porous crystalline silicate which coats the zeolite crystals to form a layer or shell over the surface of the first crystals that inactivates the surface of the crystals. A procedure of depositing an outer porous non-acidic shell on the surface of zeolite crystals is disclosed in U.S. Pat. No. 4,088,605, which is hereby incorporated by reference.

Another procedure for depositing a porous crystalline silicate layer or shell over the surface of the zeolite crystals comprises preparing an aqueous alkaline solution by mixing, preferably in the following order, an organic directing agent, such as tetrapropylammonium bromide, colloidal silica, and an alkali metal or alkaline earth metal base such as sodium hydroxide, adding the first crystals to the aqueous alkaline solution and thereafter reacting the aqueous mixture under low alkalinity crystalline conditions to produce a non-acidic porous crystalline silicate layer over the first crystals.

A preferred first zeolite is zeolite beta. Its preparation is disclosed in U.S. Pat. Nos. 3,308,069 and Re. 28,341 which are hereby incorporated by reference.

The forms of zeolite beta which are most useful as the first large pore zeolite are crystalline aluminosilicates having the empirical formula:

$$(X/n)M.(1.0\pm0.1.X)Q.AlO_2.Y\ SiO_2.W\ H_2O$$

wherein X is less than 1, preferably less than 0.75, Y is greater than 5 and less than 100, W is up to about 4, M is a metal ion, n is the valence of M, and Q is a hydrogen ion, an ammonium ion or an organic cation, or a mixture thereof. For purposes of the present invention, Y is preferably greater than 5 and less than about 50. Consequently, the silicon to aluminum atomic ratio in the above formula is greater than 5:1 and less than 100:1, and preferably greater than 5:1 and less than about 50:1.

Other elements, such as gallium, boron and iron, can be variably substituted for aluminum in the above formula. Similarly, elements such as germanium and phosphorus can be variably substituted for silicon.

Suitable organic cations are those cations which are derived in aqueous solution from tetraethylammonium bromide or hydroxide, dibenzyl-1, 4-diazabicyclo[2.2.-2]octane chloride, dimethyldibenzyl ammonium chloride, 1,4-di(1-azonium bicyclo[2.2.-2]octane)butane dibromide or dihydroxide, and the like.

M is typically a sodium ion from the original synthesis but may also be a metal added by techniques such as ion exchange or pore filling. Suitable metal cations include those from Groups IA, IIA or IIIA of the Periodic Table of Elements or a hydrogenation component. Examples of such cations include ions of lithium, potassium, calcium, magnesium, barium, lanthanum, cerium, nickel, platinum, palladium, and the like.

The second zeolite used in the zeolite bound zeolite catalyst is preferably a large pore zeolite such as a type previously described for the first zeolite. In some applications, the second zeolite will have reduced or even substantially no acid activity and which for aluminosilicate zeolites can be achieved with a high mole silica to alumina ratio. When the second zeolite is an aluminosilicate zeolite, the silica to alumina ratio of the second zeolite will depend on the structure type of the zeolite and is not limited to any particular ratio. Generally, however, and depending on the structure type of the zeolite, the second zeolite will have a silica to alumina mole ratio of at least 2:1 and for some aluminosilicate zeolites may have higher silica to alumina mole ratios, e.g., 10:1, 500:1, 1000:1, and in some applications may contain no more than trace amounts of alumina. The second zeolite is preferably present in an amount in the range of from about 10 to about 60% by weight based on the weight of the first zeolites. More preferably the amount of second zeolite present is from about 20 to about 50% by weight.

The second zeolite crystals preferably have a smaller size than the first zeolite particles. The second zeolite crystals preferably have an average particle size of less than 1 micron, preferably from about 0.1 to about 0.5 micron. The second zeolite crystals, in addition to binding the first zeolite particles and maximizing the performance of the catalyst will preferably intergrow and form an over-growth which coats or partially coats the first zeolite. Preferably the coating will be resistant to attrition.

The zeolite bound zeolite can also contain a hydrogenation component such as a catalytically active metal. Reference to the catalytically active metal or metals is intended to encompass such metal or metals in the elemental state or in some other catalytically active form such as an oxide, sulfide, halide, carboxylate and the like. Such catalytically active metals are known to persons skilled in the art and include, for example, one or more metals of Group IB, IIB, IIIA IVA, VA, VIA, IVB, VB, VIB, VIIB, and VIII of the Periodic Table of Elements. Examples of suitable metals include platinum, palladium, rhodium, iridium, iron, molydenium, cobalt, tungsten, nickel, manganese, titanium, zirconium, vanadium, hafnium, zinc, tin, lead, chromium, etc. The amount of catalytically active metal present will be an effective amount which will generally be from about 0.001 to about 10 percent by weight of the catalyst and preferably from about 0.05 to about 3.0 weight percent based on the weight of the catalyst. Processes for including a hydrogenation component in the zeolite bound zeolite catalyst are known to persons skilled in the art.

The zeolite bound zeolite catalyst can be prepared by a three step procedure, given below for the non-limiting example where the second zeolite is an aluminosilicate. The first step involves the synthesis of the first zeolite. Processes for preparing the first zeolite are known to persons skilled in the art. For example, with regard to zeolite beta, such processes are disclosed in U.S. Pat. No. 3,308,069.

After preparation of the first zeolite, a silica bound zeolite can be prepared by mixing a mixture comprising the zeolite crystals, a silica gel or sol, water and optionally an extrusion aid until a homogeneous composition in the form of an extrudable paste develops. Optionally, alumina can be included in the silica. The silica binder used in preparing the silica bound zeolite aggregate is usually a silica sol and can contain only minor amounts of alumina, e.g., less than 2 wt. %. The amount of zeolite in the extrudate when dried will range from about 40 to 90% by weight, more preferably from about 50 to 80% by weight with the balance being primarily silica, e.g. about 20 to 50% by weight silica.

The resulting paste can be molded, e.g. extruded, and cut into small strands, e.g., approximately 2 mm diameter extrudates, which can be dried at 100–150° C. for a period of 4–12 hours and then calcined in air at a temperature of from about 400° C. to 550° C. for a period of from about 1 to 10 hours.

Optionally, the silica-bound aggregate can be made into very small particles which have application in fluid bed processes such as catalytic cracking. This preferably involves mixing the zeolite with a silica containing matrix solution so that an aqueous solution of zeolite and silica binder is formed which can be sprayed dried to result in small fluidizable silica-bound aggregate particles. Procedures for preparing such aggegate particles are known to persons skilled in the art. An example of such a procedure is described by Scherzer (Octane-Enhancing Zeolitic FCC Catalysts, Julius Scherzer, Marcel Dekker, Inc. New York, 1990). The fluidizable silica-bound aggregate particles, like the silica-bound extrudates described above, would then undergo the final step described below to convert the silica binder to a second zeolite.

The final step in the three step catalyst preparation process is the conversion of the silica present in the silica-bound zeolite to the second zeolite. The first zeolite crystals are thus held together without the use of a significant amount of non-zeolite binder.

To prepare the zeolite catalyst, the silica-bound aggregate can be first aged in an appropriate aqueous solution at an elevated temperature. Next, the contents of the solution and the temperature at which the aggregate is aged should be selected to convert the amorphous silica binder into the desired second zeolite. The newly-formed second zeolite is produced as crystals. The crystals may grow on and/or adhere to the first zeolite crystals, and may also be produced in the form of new intergrown crystals, which are generally much smaller than the first crystals, e.g., of sub-micron size. These newly formed crystals may grow together and interconnect.

The nature of the zeolite formed in the secondary synthesis conversion of the silica to zeolite may vary as a function of the composition of the secondary synthesis solution and synthesis aging conditions. The secondary synthesis solution is preferably an aqueous ionic solution containing a source of hydroxy ions sufficient to convert the silica to the desired zeolite. A template, such as an organic amine, can be added to aid the conversion process. After aging, the zeolite bound zeolite is separated from solution, washed, dried and calcined.

The catalyst may be further ion exchanged as is known in the art either to replace at least in part the original alkali metal present in the zeolite with a different cation, e.g. a Group 1B to VIII Periodic Table of Elements, or to provide a more acidic form of the zeolites by exchange of alkali metal with intermediate ammonium, followed by calcination of the ammonium form to provide the acidic hydrogen form. The acidic form may be readily prepared by ion exchange using a suitable acidic reagent such as ammonium nitrate. The zeolite catalyst may then be calcined at a temperature of 400–550° C. for a period of 10–45 hours to remove ammonia and form the acidic hydrogen form. Ion exchange is preferably conducted after formation of the zeolite catalyst.

The zeolite bound zeolite catalyst finds particular application as a catalyst in hydrocarbon conversion processes involving the isomerization, alkylation, and transalkylation of aromatic hydrocarbons. Processes directed to the alkylation and transalkylation of aromatic hydrocarbons are disclosed in U.S. Pat. No. 4,891,458, which is hereby incorporated by reference.

When alkylation is the process conducted, reaction conditions are as follows. The aromatic hydrocarbon feed should be present in stroichiometric excess. It is preferred that the molar ratio of aromatics to olefins be at least about four to one (4:1) to prevent rapid catalyst fouling. The reaction temperature may range from 100° F. to 600° F., preferably, 250° to 450° F. In the case of cumene production, a temperature range of 250° F. to 375° F. is most preferred to reduce product impurities. The reaction pressure should be sufficient to maintain at least a partial liquid phase in order to retard catalyst fouling. This is typically 50 to 1000 psig depending on the feedstock and reaction temperature. Contact time may range from 10 seconds to 10 hours, but is usually from 5 minutes to an hour. The weight hourly space velocity (WHSV), in terms of grams (pounds) of aromatic hydrocarbon and olefin per gram (pound) of catalyst per hour, is generally within the range of about 0.5 to 50.

When transalkylation is the process conducted according to the invention, the molar ratio of aromatic hydrocarbon to alkylaromatic hydrocarbon will generally range from about 0.5 to about 50:1, and preferably from about 1:1 to about 20:1. The reaction temperature may range from about 100° F. to 1000° F., but it is preferably about 250° F. to 900° F. The reaction pressure is typically in the range of about 50 psig to 1000 psig, preferably 200 psig to 600 psig. The weight hour space velocity will range from about 0.1 to 10.

Examples of suitable aromatic hydrocarbon feedstocks which may be alkylated or transalkylated include aromatic compounds such as benzene, toluene, xylene, trimethylbenzene, or mixtures thereof.

Suitable olefins for the alkylation of the aromatic hydrocarbon are those containing 2 to 30 carbon atoms, such as ethylene, propylene, butene-1, trans-butene-2 and cis-butene-2, pentenes, hexenes, octenes, nomenes, decenes, undecenes, dodecenes, and tridecenes, or mixtures thereof. Preferred olefins are ethylene and propylene. These olefins may be present in admixture with the corresponding $C_2$ to $C_{30}$ paraffins, but it is usually preferable to remove dienes, acetylenes, water, sulfur compounds or nitrogen compounds which may be present in the olefin feedstock stream, to prevent rapid catalyst deactivation. In some cases, however, it may be desirable to add, in a controlled fashion, small amounts of water or nitrogen compounds to optimize catalytic properties.

When transalkylation is desired, the transalkylating agent is a alkyl-aromatic hydrocarbons containing one or more alkyl groups, e.g., 1 to 6 alkyl groups. Each group of the alkylaromatic hydrocarbon may contain from 1 to about 14 carbon atoms and preferably will contain from 1 to about 6 carbon atoms. For example, suitable alkylaromatic hydrocarbons include mono-, di-, tri- and tetra-alkyl aromatic hydrocarbons, such as methylbenzene, ethylbenzene, dimethylbenzene, trimethylbenzene, diethylbenzene, triethylbenzene, diethylmethylbenzene (diethyltoluene), diisopropylbenzene, triisopropylbenzene, diisopropyltoluene, dibutylbenzene, and the like. The transalkylation agent and the aromatic hydrocarbon that is alkalated by the transalkylation agent can be the same such as ethylbenzene and ethylbenzene reacting to form diethylbenzene and benzene.

Reaction products which may be obtained using the process of the invention include ethylbenzene from the reaction of benzene with either ethylene or polyethylbenzenes, cumene from the reaction of benzene with propylene or polyisopropylbenzenes, ethyltoluene from the reaction of toluene with ethylene or polyethyltoluenes, cymenes from the reaction of toluene with propylene or polyisopropyltoluenes, xylenes from the reaction of trimethylbenzene and toluene, and sec-butylbenzenefrom the reaction of benzene and n-butenes or polybutylbenzenes.

When conducting either alkylation or transalkylation, various types of reactors can be used in the process of this invention. For example, the process can be carried out in batchwise fashion by adding the catalyst and aromatic feedstock to a stirred autoclave, heating to reaction temperature, and then slowly adding the olefinic or alkylaromatic feedstock. A heat transfer fluid can be circulated through the jacket of the autoclave, or a condenser can be provided to remove the heat of reaction and maintain a constant temperature. Large scale industrial processes may employ a fixed bed reactor operating in an upflow or downflow mode or a moving bed reactor operating with concurrent or countercurrent catalyst and hydrocarbon flows. These reactors may contain a single catalyst bed or multiple beds and may be equipped for the interstage addition of olefins and interstage cooling. Interstage olefin addition and more nearly isothermal operation enhance product quality and catalyst life. A moving bed reactor makes possible the continuous removal of spent catalyst for regeneration and replacement by fresh or regenerated catalysts. A catalytic distillation reactor may also be used, and is especially advantageous for an alkylation reaction.

The alkylation process can be carried out with the addition of the olefin in at least two stages. Preferably, there will be two or more catalyst beds or reactors in series, wherein at least a portion of the olefin is added between the catalyst beds or reactors. Interstage cooling can be accomplished by the use of a cooling coil or heat exchanger. Alternatively, interstage cooling can be effected by staged addition of the aromatic feedstock, that is, by addition of the aromatic feedstock in at least two stages. In this instance, at least a portion of the aromatic feedstock is added between the catalyst beds or reactors, in similar fashion to the staged addition of olefin described above. The staged addition of aromatic feedstock provides additional cooling to compensate for the heat of reaction.

In a fixed bed reactor or moving bed reactor, alkylation is completed in a relatively short reaction zone following the introduction of olefin. Ten to thirty percent of the reacting aromatic molecules may be alkylated more than once. Transalkylation is a slower reaction which occurs both in the alkylation zone and in the remainder of the catalyst bed. If transalkylation proceeds to equilibrium, better than 90 wt. % selectivity to monoalkylated product can be achieved.

The alkylation reactor effluent contains excess aromatic feed, monoalkylated product, alkylated products, and various impurities. The aromatic feed is recovered by distillation and recycled to the alkylation reactor. Usually, a small purge stream is taken from the recycle stream to eliminate unreactive impurities from the loop. The bottoms from the benzene distillation are further distilled to separate monoalkylated product from alkylated products and other heavies. In most cases, the recovered monoalkylated product must be very pure. For example, current specifications call for 99.9% cumene purity with less than 500 ppm each of ethylbenzene and butylbenzene. Since only a small fraction of by-product ethylbenzene and n-propylbenzene can be economically removed by distillation, it is important to have a feedstock containing very little ethylene and a catalyst which makes very little of the impurities.

Additional monoalkylated product may be produced by transalkylation. The alkylated products may be recycled to the alkylation reactor to undergo transalkylation or they may be treated with additional aromatic feed in a separate reactor. Usually, it is preferred to blend the bottoms from the distillation of monoalkylated product with a stoichiometric excess of the aromatic feed, and react the mixture in a separate reactor over a suitable transalkylation catalyst. The effluent from the transalkylation reactor is blended with alkylation reactor effluent and the combined stream distilled. A purge stream may be taken from the alkylated product stream to remove unreactive heavies from the loop or the alkylated product stream may be distilled to remove heavies prior to transalkylation.

When isomerization is the process conducted, the aromatic hydrocarbon feed employed will comprise isomerizable monocyclic alkylaromatic hydrocarbons that preferably contain from two to three alkyl group substituents on the ring, isomerizable bicyclic alkylaromatic hydrocarbons that preferably contain from two to four alkyl group substituents on the rings. These hydrocarbons include:

(A) monocyclic alkylaromatic hydrocarbons represented by the formula:

I.

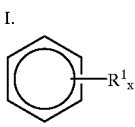

wherein:

$R^1$ is a alkyl group having 1 to about 4 carbon atoms; and,

X is integer of from 2 to 3 and equals the number of alkyl groups;

(B) bicyclic alkylaromatic hydrocarbons represented by the formula:

II.

wherein

R² and R³ are independently selected from an alkyl group having 1 to about 4 carbon atoms:

Y is an integer of from 0 to 2;

Z is an integer of from 0 to 2;

wherein the sum of Y and Z is an integer in the range of from 1 to 4 and equals total the number of alkyl groups.

$R^1$, $R^2$, and $R^3$ can be straight or branch chained alkyl groups. Examples of suitable alkyl groups include methyl, ethyl, n-propyl, n-butyl, isopropyl, isobutyl, or any combination thereof. The preferred group is methyl.

Suitable monocyclic alkylaromatic hydrocarbons include, for example, xylenes such as para-xylene, ortho-xylene, and meta-xylene, diethylbenzenes such as 1,4-diethylbenzene, 1,2-diethylbenzene, and 1,3-diethylbenzene, trimethylbenzenes such as mesitylene (1,3,5-trimethylbenzene), hemimellitene (1,2,3-trimethylbenzene), and pseudocumene (1,2,4-trimethylbenzene), ethyltoluenes, triethylbenzenes such as 1,3,5-triethylbenzene, methylpropylbenzenes, ethylpropylbenzenes, dipropylbenzenes, diisopropylbenzenes, triisopropylbenzenes, etc., and mixtures thereof. Suitable bicyclic alkylaromatic hydrocarbons include monoalkynaphthalenes such as 1-methylnaphthalene and 3-ethylnaphthalenes, dialkylnaphthalenes such as 1,2-dimethylnaphthalene, 1,2-diethylnaphthalene 2,3-dimethylnaphtha-lene, 2,3-dipropylnaphthalene 2,6-dimethylnaphthalene, 2,6-dibutyl-naphthalene, and the like.

The alkylaromatic hydrocarbon feed may consist only of the monocyclic alkylaromatic hydrocarbons having 2 to 3 alkyl groups on the ring and/or the bicyclic alkylaromatic hydrocarbons or may also include other aromatic hydrocarbons such as ethylbenzene and toluene.

The process of the present invention finds particular application for isomerizing one or more xylene isomers in a $C_8$ aromatic feed to obtain ortho-, meta-, and para-xylene in a ratio approaching the equilibrium value. In particular, xylene isomerization is used in conjunction with a separation process to manufacture para-xylene. For example, a portion of the para-xylene in a mixed $C_8$ aromatics stream may be recovered using processes known in the art, e.g., crystallization, adsorption, etc. The resulting stream is then reacted under xylene isomerization conditions to restore ortho-, meta-, and paraxylenes to a near equilibrium ratio. At the same time, it is also desirable that ethylbenzene in the feed be converted with very little net loss of xylenes. In this application, the zeolite bound zeolite catalyst will contain a hydrogenation/dehydrogenation component such as platinum to hydrogenate ethene formed during the deethylation of the ethylbenzene and thereby reduce the formation of ethylated products. The acidity of the first zeolite and second zeolite of the zeolite bound zeolite catalyst can be selected to balance xylene isomerization and ethylbenzene dealkylation while minimizing undesirable side reactions. The isomerization process is carried out by contacting a $C_8$ aromatic stream containing one or more xylene isomers or ethylbenzene or mixtures thereof, under isomerization conditions with the zeolite bound zeolite catalyst.

In the vapor phase, suitable isomerization conditions include a temperature in the range of 250° C.–600° C., preferably 300° C.–550° C., a pressure in the range 0.5–50 atm abs, preferably 10–25 atm abs, and a weight hourly space velocity (WHSV) of 0.1 to 100, preferably 0.5 to 50. Optionally, isomerization in the vapor phase is conducted in the presence of 0.1 to 10.0 moles of hydrogen per mole of alkylbenzene. If hydrogen is used, the catalyst should comprise 0.01 to 2.0 wt. % of a hydrogenation/dehydrogenation component selected from Group VIII of the Periodic Table, especially platinum, palladium, or nickel. By Group VIII metal component is meant that the metals and their compounds such as oxides and sulfides.

The following examples illustrate the invention:

EXAMPLE 1

Preparation of Catalyst A—Mordenite bound mordenite.

Mordenite was formed into silica bound particles as follows:

| Components Used for Preparation | Quantity (Grams) |
| --- | --- |
| Silica Sol (Nalcoag 1034) | 197.20 |
| Silica H₂O Gel (Aerosil 300) | 18.50 |
| Water | 105.81 |
| Zeolite Na-Mordenite crystals (sodium form) | 200.05 |
| Methocel (Hydroxypropyl methyl cellulose extrusion acid) | 1.30 |

The above components were mixed in a household mixer in the order shown. After adding the methocel, a thickened dough was obtained. The total mixing time was about 24 minutes.

The dough was broken into 2 cm pieces, dried at 120° C. and crushed and sieved to a sieve fraction between 1 and 2 mm. The sieved fraction was calcined at 510° C. for 8 hours in air.

Composition of silica-bound calcined particles:

Mordenite: 69.95 wt. %

$SiO_2$: 30.05 wt. %

The silica-bound mordenite particles was converted into mordenite bound by mordenite as follows:

| Components Used for Preparation | Quantity (grams) | Comment Number |
| --- | --- | --- |
| NaAlO₂ | 2.48 | 1 |
| NaOH (98.6%) | 1.36 | 2 |
| Water | 72.62 | 3 |
| Rinse Water | 40.10 | 4 |
| Tetraethylammonium hydroxide (40%) | 14.16 | 5 |

Components 1 and 2 were dissolved in a beaker containing component 3 to form a solution and water loss was corrected. The solution was poured into a 300 ml stainless steel autoclave. Component 4 was used to rinse the beaker and poured into the autoclave. Next, component 5 was added to the contents of the autoclave and the contents were stirred. Finally, 80 grams of the silica bound particles were added to the contents of the autoclave. The particles were covered by the liquid. The molar composition of the synthesis mixture was:

0.79 Na$_2$O/0.48 (TEA)$_2$O/0.33 Al$_2$O$_3$/10SiO$_2$/169 H$_2$O

The autoclave was placed in an oven and heated up to 150° C. in 2 hours and kept at this temperature for 96 hours. After the aging period, the autoclave was opened and the products were collected.

The product was washed 7 times with 1400 ml of water at 60° C. to a pH of 11.3. The conductivity of the last wash water was 75 µS/cm. The product was then dried overnight at 120° C. and subsequently calcined in air for 20 hours at 500° C. The amount of product recovered was 75.8 grams.

The product extrudates were characterized by x-ray diffraction (XRD) and scanning electron microscopy (SEM) with the following results:

XRD: Showed typical patterns for mordenite and excellent crystallinity.

SEM: 2500 times Micrographs (FIG. 1) show that the mordenite crystals are intergrown and coated with submicron crystals.

Elemental:
Core crystals: Si/Al$_2$O$_3$=12.4
Binder crystals: Si/Al$_2$O$_3$ (expected value by calculation)=23

EXAMPLE 2

Preparation of Catalyst B—Zeolite Beta bound by Zeolite Beta.

Zeolite beta (sodium form and a silica to alumina mole ratio of 12.4) was formed into silica bound extrudates as follows:

| Components Used for Preparation | Quantity (Grams) |
|---|---|
| Beta zeolite crystals | 300.00 |
| SiO$_2$ gel (aerosil 300) | 11.5 |
| Silica sol (Nyacol 2034 DI) | 346.2 |
| Water | 70.7 |
| Methocel | 2.3 |

The components were mixed in the order listed. Total mixing time was about 28 minutes. A plastic extrudable dough was obtained. The dough was extruded into approximately 2 mm extrudates. The extrudates were dried overnight at 120° C. and then calcined for 8 hours at 510° C.

Composition of the calcined silica-bound extrudate:

Beta=69.90 wt. %
SiO$_2$=30.05 wt. %

The silica bound extrudates were converted to zeolite beta bound by zeolite beta as follows:

| Components Used for Preparation | Quantity, (Grams) | Component No. |
|---|---|---|
| NaAlO$_2$ | 1.55 | 1 |
| Tetraethylammonium hydroxide (40%) | 33.36 | 2 |
| Water | 51.66 | 3 |
| Rinse Water | 18.33 | 4 |

Components 1 and 2 were dissolved in a beaker at room temperature with component 3 to form a solution. The solution was poured into a 300 ml stainless steel autoclave. Component 4 was used to rinse the beaker and then added to the contents of the autoclave. The contents of the autoclave were stirred and finally 50.00 grams (dry wt.) of beta crystals were added to the contents of the autoclave. The molar composition of the synthesis mixture was:

0.37 Na$_2$O/3.63 TEAOH/0.32 Al$_2$O$_3$/10 SiO$_2$/223 H$_2$O

The autoclave was placed into an oven at room temperature. The oven was heated in 2 hours to 150° C. and then maintained at 150° C. for 72 hours. The resulting product was washed 8 times at 60° C. with 150 ml of water. The conductivity of the last wash water was 48 µS/cm. The product was dried overnight at 120° C. and then calcined in air at 500° C. for 20 hours. The amount of product recovered was 55.26 grams.

The product was analyzed by XRD and SEM with the following results:

XRD: Showed typical patterns for zeolite beta and excellent crystallinity.

Figure 2:
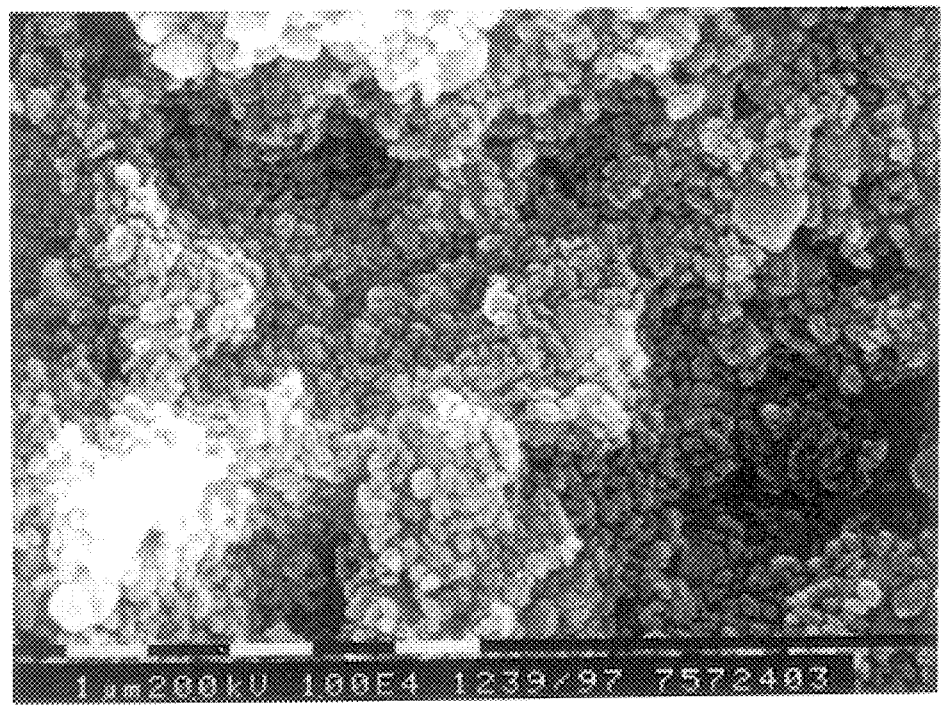
FIG. 2 shows SEM micrographs of the Catalyst of Example 2.

SEM: 10,000 times Micrographs (FIG. 2) show the Beta crystals are coated with newly formed crystals having a submicron size.

Elemental:
Core crystals SiO$_2$/Al$_2$O$_3$=26
Binder crystals SiO$_2$/Al$_2$O$_3$=26

Core crystals=70 wt. %
Binder crystals=30 wt. %

EXAMPLE 3

Catalyst B was tested for the alkylation of benzene using 1-dodecene as the alkylation agent. Prior to use, Catalyst B was treated three times with a 5 fold weight excess of 1.0 N aqueous ammonium nitrate at 70° C. Next, Catalyst B was washed with de-ionized water until the conductivity of the last wash water was less than 75 µSCM and then dried over night at 70° C. Finally, Catalyst B was heated from 35° C. to 435° C., in about 3½ hours, held for 2 hours at 435° C., and then held for 5 hours at 510° C. ICPES analysis showed a sodium content of the catalyst to be 83 ppm.

The test was carried out by drying 1.12 grams of Catalyst B for 1 hour at 200° C. Next, Catalyst B was cooled with a nitrogen feed to 65° C. After cooling, 10.6 grams of decane, 5.89 grams of benzene, and 2.12 grams of 1-dodecene were added to the feed under nitrogen with stirring. Samples were taken at various intervals and were analyzed by gas chromatography.

Tests were also conducted using a commercially available alumina bound H-Beta zeolite catalyst (30 wt. % alumina and SiO$_2$/Al$_2$O$_3$=11:1) The tests followed the same procedure used for Catalyst B. The products of the reaction were dodecylbenzene with attachment of the phenyl group at different positions along the C$_{12}$ chain. Product selectivities (based on total alkylated products) and 1-dodecene conversion are shown below in Table 1:

TABLE I

Product Selectivities

| Catalyst | Time on Stream (h) | Dodecene Conversion (%) | 2-alkyl (%) | 3-alkyl (%) | 4-alkyl (%) | 5-alkyl (%) | 6-alkyl (%) | Di-alkyl (%) |
|---|---|---|---|---|---|---|---|---|
| B | 0.50 | 9.9 | 60.3 | 23.3 | 8.6 | 3.4 | 4.3 | <0.1 |
| B | 2.25 | 29.3 | 55.5 | 23.9 | 9.7 | 5.3 | 5.6 | <0.1 |
| B | 3.47 | 31.4 | 54.1 | 24.3 | 10.2 | 5.7 | 5.7 | <0.1 |
| B | 4.67 | 37.5 | 52.6 | 24.6 | 10.3 | 6.0 | 6.5 | <0.1 |
| Alumina Bound | 0.63 | 53.5 | 52.9 | 23.4 | 10.4 | 6.9 | 6.4 | <0.1 |
| Alumina Bound | 1.60 | 55.2 | 48.6 | 23.7 | 11.3 | 7.5 | 8.9 | <0.1 |
| Alumina Bound | 2.88 | 65.7 | 45.8 | 23.9 | 11.8 | 8.6 | 9.9 | <0.1 |
| Alumina Bound | 4.68 | 79.7 | 41.5 | 22.6 | 11.6 | 14.3 | 10.0 | <0.1 |

EXAMPLE 4

An amount of 5.5 grams of Catalyst B was tested for benzene alkylation with ethylene. The test was carried out using the following procedure: 5.5 grams of catalyst were placed into the middle of a catalyst basket formed of 2 concentric cylinders of steel mesh. The remainder of the basket was filled with inert 3A zeolite $\frac{1}{16}$" extrudate. Next, the basket was located in a 300 cc stirred (750 rpm) autoclave reactor. A feed comprising benzene (54.6 g/h), ethylene (68.9 std mL/min) and hydrogen (73.3 std mL/min) was fed to the reactor. The temperature of the reactor was 180° C. and the length of the run was 16 hours. The liquid and gas streams were analyzed periodically by a gas chromatograph.

A test was also run using the commercially available alumina bound Beta Zeolite identified in Example 3 was also tested. The test followed the same procedure as Catalyst B, except that since the aluminum bound catalyst had higher activity because of a higher $SiO_2/Al_2O_3$ ratio, the following adjustments were made in order to provide a relevant comparison between the 2 catalysts, ethylene was fed at 86.6 std mL/min and hydrogen was fed at 46.7 std mL/min.

The results of these tests are shown below in Table II:

TABLE II

| Example | Catalyst | P ($C_2^-$) | R | % Ethane | % EB | % 2EB | % 3EB | % 4EB |
|---|---|---|---|---|---|---|---|---|
| 1 | Catalyst B | 29.6 | 14.8 | 0.5 | 79.2 | 17.9 | 2.2 | 0.1 |
| 2 | Commercial | 23.3 | 32.8 | 0.2 | 67.8 | 26.3 | 5.2 | 0.4 |

Selectivity on Ethylene

P($C_2^-$) is the calculated partial pressure of ethylene in pounds per share inch absolute
R is ethylene consumption in millimoles ethylene/hour/gram/catalyst The data shows that Catalyst B had good ethylene selectivity.

EXAMPLE 5

Catalyst A and a commercially available alumina bound mordenite catalyst were tested for transalkylation of aromatics using a model feed containing 34 wt. % toluene, 17 wt. %, 1,3,5-trimethylbenzene, 41 wt. % 1,2,4-trimethylbenzene, and 1,2,3-trimethylbenzene.

The tests were carried out by mixing 4.5 grams of the catalyst with 4.5 grams of quartz and then loading it into a 0.5 inch diameter stainless steel reactor. The total length of the reactor was 5 inches. The reactor was equipped with an axial thermo-well to measure the actual bed temperature. Catalyst de-edging was carried out for 12.5 minutes at 716° F., pressure (psig) of 72.5, hydrogen flow rate (cc/min) of 705 and a model feed flow rate (gram/hour) of 8.5. After de-edging, the catalyst was hydrogen stripped for 1 hour at 716° F. and a hydrogen flow rate (cc/min) of 335 and a pressure (psig) of 72.5. After the hydrogen strip, the model feed was introduced into the hydrogen stream. The initial run was 1 hour at 716° F. and after 3 hours time on stream (TOS), the temperature was increased to 892° F. The conditions and results of the tests are shown below in Tables III.

TABLE III

| | Catalyst A | | Alumina Bound Morderite | |
|---|---|---|---|---|
| | Test 1 | Test 2 | Test 1 | Test 2 |
| Temperature (° F.) | 716 | 892 | 716 | 892 |
| TOS (hrs) | 0.75 | 4 | 0.75 | 4 |
| H$_2$/HC molar ratio | 11 | 11 | 11 | 11 |
| Pressure (psig) | 72.5 | 72.5 | 72.5 | 72.5 |
| WHSV (hr-1) | 1.9 | 1.9 | 1.9 | 1.9 |
| Toluene conversion (wt. %) | 41.9 | 56.4 | 27.1 | 17.9 |
| Total A$_8$ aromatics yield (wt. %) | 37.3 | 35.7 | 22.3 | 9.8 |
| Cumulative A$_8$ yield (grams A$_8$/grams cat) | 0.6 | 2.11 | 0.46 | 0.96 |

The data shows that Catalyst A had higher activity and higher xylene selectivity than the alumina bound mordenite catalyst.

What is claimed is:

1. A process for the alkylation of aromatic hydrocarbons which comprises contacting a feedstream containing aromatic hydrocarbon and at least one olefin under alkylation conversion conditions with a zeolite bound zeolite catalyst which does not contain significant amounts of non-zeolitic binder and comprises:

(a) first crystals of a first large pore zeolite; and,
   (b) a binder comprising of a second crystals of second zeolite.

2. The process recited in claim 1, wherein said second crystals are intergrown and form at least a partial coating on said first crystals.

3. The process recited in claim 2, wherein said first crystals of said first zeolite have an average particle size greater than about 0.1 micron and said second crystals of said second zeolite have an average particle size that is less than said first crystals of said first zeolite.

4. The process recited in claim 3, wherein said aromatic hydrocarbon is benzene, toluene, xylene, or mixtures thereof.

5. The process recited in claim 4, wherein said first zeolite and said second zeolite are independently selected for the group consisting of MAZ, MEI, AFI, EMT, OFF, BEA, and MOR.

6. The process recited in claim 5, wherein said first zeolite is an aluminosilicate zeolite or a gallium silicate zeolite.

7. The process recited in claim 6, wherein said olefin is ethylene, propylene, butene-1, trans-butene-2 and cis-butene-2, pentene, hexene, octene, nomene, decene, undecene, dodecene, tridecene, or mixtures thereof.

8. The process recited in claim 2, wherein said second zeolite has the same structure as said first zeolite.

9. The process recited in claim 5, wherein said conversion conditions include a temperature from about 100° F. to about 1000° F., a pressure from 50 to about 1000 psig, and a weight hourly space velocity from about 0.5 to about 50.

10. The process recited in claim 7, wherein said feedstream has a molar ratio of aromatic hydrocarbons to olefins of at least 4:1.

11. The process recited in claim 10, wherein said aromatic hydrocarbon is benzene.

12. The process recited in claim 11, wherein said olefin is ethylene, propylene, butene-1, trans-butene-2 and cis-butene-2, pentene-1, hexene-1.

13. The catalyst recited in claim 6, wherein said first zeolite is an aluminosilicate zeolite and has a silica to alumina mole ratio from 2:1 to about 150:1.

14. The catalyst recited in claim 8, wherein the average particle size of the crystals of said first zeolite is from about 1 to about 6 microns and the average particle size of the crystals of said second zeolite is from about 0.1 to about 0.5 microns.

15. A process for the transalkylation of aromatic hydrocarbons which comprises contacting under transalkylation conversion conditions, an aromatic hydrocarbon feedstream containing a alkylaromatic hydrocarbon having from 1 to about 6 alkyl groups of from 1 to about 14 carbon atoms with a zeolite bound zeolite catalyst which does not contain significant amounts of non-zeolitic binder and comprises:
   (a) first crystals of a large pore first zeolite; and,
   (b) a binder comprising of a second crystals of second zeolite.

16. The process recited in claim 15, wherein said second crystals are intergrown and form at least a partial coating on said first crystals.

17. The process recited in claim 16, wherein said first crystals of said first zeolite have an average particle size greater than about 0.1 micron and said second crystals of said second zeolite have an average particle size that is less than said first crystals of said first zeolite.

18. The process recited in claim 17, wherein said alkylaromatic hydrocarbon is toluene, ethylenebenzene dimethylbenzene, trimethylbenzene, diethylbenzene, triethylbenzene, diethylmethylbenzene, diisopropylbenzene, triisopropylbenzene, diisopropyltoluene, dibutylbenzene or mixture thereof.

19. The process recited in claim 18, wherein said first zeolite and said second zeolite are independently selected for the group consisting of MAZ, MEI, AFI, EMT, OFF, BEA, and MOR.

20. The process recited in claim 19, wherein said first zeolite is an aluminosilicate zeolite or a gallium silicate zeolite.

21. The process recited in claim 20, wherein said second zeolite has the same structure as said first zeolite.

22. The process recited in claim 21, wherein said conversion conditions include a temperature from about 100° F. to 1000° F., a pressure from 50 to about 1000 psig, and a weight hourly space velocity from 0.1 to 100.

23. The process recited in claim 22, wherein said feedstream has a molar ratio of aromatic hydrocarbon to be alkylated to alkylaromatic hydrocarbon in the range of from about 0.5:1 to about 50:1.

24. The process recited in claim 23, wherein said alkylaromatic hydrocarbon is toluene, dimethylbenzene, trimethylbenzene or mixtures thereof.

25. The process recited in claim 21, wherein said first zeolite is an aluminosilicate zeolite and has a silica to alumina mole ratio from 2:1 to about 300:1.

26. The process recited in claim 25, wherein the average particle size of the crystals of said first zeolite is from about 1 to about 6 microns and the average particle size of the crystals of said second zeolite is from about 0.1 to about 0.5 microns.

27. The process recited in claim 26, wherein said catalyst contains less than 5% by weight of non-zeolitic binder based on weight of said first zeolite and said second zeolite.

28. The process recited in claim 20, wherein said first zeolite is BEA or MAZ.

29. The process recited in claim 20, wherein said second zeolite is a BEA or MAZ.

30. The process recited in claim 20, wherein said first zeolite is an aluminosilicate zeolite and has a silica to alumina ratio from 2:1 to about 150:1.

31. A process for isomerizing a feed containing isomerizable monocyclic alkylaromatic hydrocarbons, bicyclic alkylaromatic hydrocarbons, or mixtures thereof comprising:
    contacting said feed under isomerization conversion conditions with a zeolite bound zeolite catalyst which does not contain significant amounts of non-zeolitic binder and comprises:
    (a) first crystals of a first large pore size zeolite;
    (b) a binder comprising second crystals of a second zeolite.

32. The process recited in claim 31, wherein said second crystals are intergrown and form at least a partial coating on said first crystals.

33. The process recited in claim 32, wherein said first crystals of said first zeolite have an average particle size greater than about 0.1 micron and said second crystals of said second zeolite have an average particle size that is less than said first crystals of said first zeolite.

34. The process recited in claim 33, wherein said alkylaromatic hydrocarbons are selected from the group consisting of:
    (a) a monocyclic alkylaromatic hydrocarbon represented by the formula:

I.

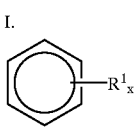

wherein:
R$^1$ is a alkyl group having 1 to about 4 carbon atoms; and
X is an integer of from 2 to 3; and (b) a bicyclic alkylaromatic hydrocarbon represented by the formula:

II.

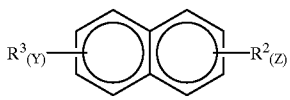

wherein
$R^2$ and $R^3$ are independently selected from an alkyl group having 1 to about 4 carbon atoms:
Y is an integer of from zero to 2;
Z is an integer of from zero to 2;
wherein the sum of Y and Z is an integer in the range of from 1 to 4; and,
(c) mixtures thereof.

35. The process recited in claim 34, wherein the structure type of said first zeolite and said second zeolite are independently selected from the group consisting of MAZ, MEI, AFI, EMT, OFF, BEA, and MOR.

36. The process recited in claim 35, wherein said feed comprises monocyclic alkylaromatic hydrocarbons.

37. The process recited in claim 36, wherein $R^1$ is methyl or ethyl and x is 2.

38. The process recited in claim 35, wherein said alkylaromatic hydrocarbon comprises bicyclic alkylaromatic hydrocarbons.

39. The process recited in claim 38, wherein $R^2$ and $R^3$ are methyl, y is 1 and z is 1.

40. The process recited in claim 36, wherein said feed is an aromatic $C_8$ mixture of ethylbenzene and xylene in which the paraxylene is less than at thermodynamic equilibrium.

41. The process recited in claim 35, wherein said first zeolite is an aluminosilicate zeolite.

42. The process recited in claim 41, wherein said first zeolite is at least partially in the hydrogen form.

43. The process recited in claim 42, wherein said zeolite bound zeolite catalyst further comprises at least one hydrogenation metal.

44. The process recited in claim 41, wherein said isomerization conditions comprise a temperature in the range of from about 250° to about 600° C., a pressure in the range of from about 0.2 to about 50 atm abs, a weight hour space velocity of from about 0.1 to about 100, and a $H_2$/HC molar ratio of between 0.1 to about 10.

45. The process recited in claim 44, wherein said second zeolite has less acidity than said first zeolite.

46. The process recited in claim 45, wherein said first crystals have an average particle size of from about 1 to about 6 microns.

47. The process recited in claim 46, wherein said first zeolite is a aluminosilicate zeolite and has a silica to alumina ratio from 2:1 to about 150:1.

48. The process recited in claim 47, wherein said catalyst contains less than 5% by weight of non-zeolitic binder based on weight of said first zeolite and said second zeolite.

49. The process recited in claim 48, wherein said first zeolite is a MOR structure.

50. The process recited in claim 49, wherein said second zeolite is a BEA.

51. The process recited in claim 41, wherein said second crystals of said second zeolite are present in an amount in the range of from about 10 to about 60% by weight based on the weight of the first zeolite.

* * * * *